US006465191B1

(12) United States Patent
Stefas et al.

(10) Patent No.: US 6,465,191 B1
(45) Date of Patent: *Oct. 15, 2002

(54) PROCESS FOR SEPARATING AND/OR DETECTING AND/OR QUANTIFYING (AN) INFECTIOUS COMPOUND(S) AND SUPPORT FOR IMPLEMENTING THE PROCESS

(75) Inventors: Elie Stefas, la Grande-Motte; Marcell Rucheton, Montpellier; Hubert Graafland, Montpellier; Francisco Veas, Montpellier, all of (FR)

(73) Assignee: Institut Francais de Recherches Scientifiques Pour le Developpement en Cooperation-Orstom, Paris (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/791,708

(22) Filed: Jan. 31, 1997

(30) Foreign Application Priority Data

Aug. 1, 1994 (FR) .............................. 94 09529
Aug. 1, 1994 (FR) .............................. 94 09528

(51) Int. Cl.$^7$ .......................... C12Q 1/70; A61K 39/29
(52) U.S. Cl. .......................... 435/7.1; 435/5; 435/7.92; 436/518; 436/531; 530/350
(58) Field of Search ............... 435/7.1, 5, 7.92; 436/518, 531; 530/350

(56) References Cited

U.S. PATENT DOCUMENTS 5,344,758 A * 9/1994 Krilis et al. ............... 433/4.1
5,472,883 A * 12/1995 Matsuura et al. .......... 436/518
5,650,269 A * 7/1997 Rucheton et al. .......... 435/5

FOREIGN PATENT DOCUMENTS

| EP | 124 896 | 11/1984 |
| EP | 600 088 | * 5/1994 |
| EP | 600 088 | 6/1994 |
| FR | 2 701 319 | 8/1994 |
| WO | 91/02816 | 3/1991 |
| WO | 92/19755 | 11/1992 |

OTHER PUBLICATIONS

Mehdi et al.(YR) J. Virol. 68(4): 2415–2424, Apr. 1994.*
Galli et al. Lancet 335: 1544–1547, 1990.*
Mehdi et al: "Hepatities B Virus Surface Antigen Binds to Apolipoprotein H", Journal of Virology, Apr. 1994, vol. 68, No. 4, pp. 2415–1424.
Lozier et al: "Complete amino acid sequence of human plasma beta 2 glycoprotein I", Proc. Nactl. Acad. Sci., vol. 81, Jun. 1984, pp. 3640–3644.

* cited by examiner

Primary Examiner—Mary K. Zeman
(74) Attorney, Agent, or Firm—Nixon & Vanderhye

(57) ABSTRACT

Method for separating and/or screening and/or quantifying one or more infectious compounds (IC) in a biological material, characterised in that a β2GPLIC complex, chosen from the group comprising a) (β2GPI)n/IC complexes and b) (β2GPI)r/nVIC (non viral IC) complexes, is separated and/or screened and/or quantified.

54 Claims, No Drawings

PROCESS FOR SEPARATING AND/OR DETECTING AND/OR QUANTIFYING (AN) INFECTIOUS COMPOUND(S) AND SUPPORT FOR IMPLEMENTING THE PROCESS

This application claims priority to application No. 94/09528, filed Aug. 1, 1994 in France and application No. 94/09529, filed Aug. 1, 1994 in France.

The present invention relates to a process for separating and/or detecting and/or quantifying (an) infectious compound(s) in a biological material and to a support for implementing the process.

According to the present invention, infectious compounds, generically referred to below in abbreviated form by "IC", are understood to mean both compounds, in particular proteinaceous compounds, which are constituents of an infectious agent and structures which include infectious compounds. These structures are, in particular, either complete or incomplete, endogenous or exogenous infectious agents, their metabolites or else assemblies which contain constituent compounds of these infectious agents, which assemblies exhibit certain properties of said infectious agents, in particular the property of being detected by certain antibodies which are specific for infectious compounds; the IC's can also be compounds which are specifically induced in the organism by the previously defined IC's or by the expression of genes which are being expressed in an abnormal manner. IC's which may be mentioned, for example, are viruses, bacteria, fungi, mycoplasmas, parasites and abnormal animal cells. A viral infectious compound will be designated below by "VIC" while a non-viral infectious compound, that is to say an infectious compound of a type other than solely viral, will be designated by "nVIC".

"Biological material" is understood here to be a biological tissue, a liquid or solid preparation or extract derived from biological tissue, or a natural medium which is capable of containing an infectious compound in the above-defined sense (for example, drainage water). The material can also be a mixture of at least two materials as defined above. Such a biological material can, therefore, be, in particular, either prepared from tissues, organs, stools or biological liquids from a patient who is suffering from an infection, for example a viral, a bacterial, a parasitic, a mycotic or a mycoplasma infection, or obtained from "in-vitro" cultures; such a biological material can also be a serum, plasma, urine, cerebrospinal fluid, synovial fluid, peritoneal fluid, pleural fluid, seminal fluid or ascitic fluid.

It is known that β2-glycoprotein I, abbreviated "β2GPI" below, is a plasma glycoprotein whose sequence has been demonstrated, in particular, in the papers by J. LOZIER et al., Proc. Natl. Acad. Sci. ISA [sic], Vol. 81, pages 3640–3644, July 1984 and T. KRISTENSEN et al., FEBS Letters, Vol. 289, 1991, pages 183–186. β2GPI is also termed apolipoprotein H. It has been established that this protein exhibits a polymorphism: the name β2GPI will be regarded below as being generic for all the forms.

It has been shown in International Application WO 94/18569 that some viral compounds bind specifically to one form of β2GPI, namely that which is described in French Patent Application 2 701 263, whether this form of β2GPI is in a pure state or contained in a protein composition; this form of β2GPI is isolated from the residue which is bound to the affinity chromatography column(s) which is/are employed in the process for purifying albumin from blood plasma which is described in FR-A-2 690 444; it has a molecular weight of 50,000±3000 daltons; in the context of the present patent application, this form of β2GPI has been designated in abbreviated form "β2'GPI". A process has therefore been proposed in WO 94/18569 for detecting and/or assaying viral compounds, in which the viral compounds (VIC's) are bound using β2'GPI. In such a process, the β2'GPI is therefore added to the VIC's which are contained in a biological material in such a way as to separate the VIC's which have thus been captured in order then to detect them and/or assay them.

In a general manner, a direct or indirect association between at least one IC and one β2GPI will be termed here "(a) complex(es)": in a general manner, these complexes will be referred to below by the notation "β2GPI/IC". The process described in WO 94/18569 detects and/or assays VIC/β2'GPI complexes between VIC viral compounds and β2'GPI which is either in a pure state or contained in a protein composition, with the β2'GPI being added to the biological material which contains the VIC's to be detected and/or assayed.

The form or forms of β2GPI which is/are naturally present in the biological material prior to implementing the process described below, and not intentionally added as such, will be designated here (β2GPI)n. The form or forms of β2GPI which are added intentionally in order to form the previously defined IC/β2GPI complexes will be designated (β2'GPI)a.

According to the present invention, it was found, in a novel manner, that it was possible to separate, detect and/or quantify other IC/β2GPI complexes from a biological material than those described in WO 94/18569, namely:

(β2GPI)n/IC complexes where the IC part can be of the VIC viral type or the nVIC non-viral type and the (β2GPI)n part derives naturally from the biological material under study, (β2GPI)a/nVIC complexes where the (β2GPI)a part is added intentionally and prepared in different pure or mixed forms for this purpose, and the nVIC part derives from non-viral infectious compounds in the biological material under study.

The present invention relates, therefore, to a process for separating and/or detecting and/or quantifying infectious compounds (IC's) in a biological material, characterized in that a β2GPI/IC complex selected from the group formed by:
a) the (β2GPI)n/IC complexes
b) the (β2GPI)a/nVIC complexes
is separated and/or detected and/or quantified.

In a general manner, the β2GPI, like the IC's, can, for some applications of the process, be of animal origin or produced by genetic and/or chemical engineering. The process can be applied both to man and to animals.

According to the invention, the β2GPI part of the complexes will be identified by its being recognized with the aid of (a) substance(s) which may bind preferentially, or which binds specifically, to this part, and the IC part will be identified by any suitable means.

The formation of the complexes can be direct or indirect and can be mediated or promoted by certain additives, which can be chemical, biochemical or biological, such as certain lipids or detergents, in particular phospholipids. The complexes can be formed during the preparation of the biological material and/or during one (of the) stages of the process.

As previously pointed out, the IC's comprise the VIC's and the nVIC's. The VIC's which may in particular be mentioned are those of the group formed by HIV1, HIV2, HBV, HSV and particles or proteins of viral origin; those nVIC's which may in particular be mentioned are those of the group formed by bacteria, parasites, fungi and mycoplasmas and, more specifically: in the case of bacteria: Borellia; and in the case of parasites: Leishmania, infantum in particular, Toxoplasma gondii and Entamoeba histolytica.

Advantageously, the β2GPI which is retained in the complex(es) may or may not, according to the embodiments of the process, have been labeled; this labeling, which may or may not take place beforehand, can be effected, for example, by means of an antibody, an enzyme, a radioactive product, a fluorescent product or a metallic agent.

According to the present invention, a poly-specific test which is able to detect different infectious agents can be carried out using, in particular, simultaneously or successively, a different detection method for each agent, for example an alkaline phosphatase-conjugated antibody against HIV2p26 and then a peroxidase-conjugated antibody against HBsAg.

In a first subset of embodiments of the present invention, in which an external (β2GPI)a is added to the biological medium, use can be made of β2'GPI, which is pure or is in the form of a protein composition which contains, in particular, other glycoproteins, as the β2GPI form for the β2GPI part of the complex; this composition can, in particular, be that which is obtained by eluting a gel affinity column which carries sulfate groups, as described in French Patent Application 2 701 263. However, other forms of β2GPI may also be employed, for example that obtained in accordance with the protocol described by J. Arvieux et al. in Journal of Immunological Methods (1991), 143, pp. 223–229. Carbamylated β2GPI is able to form some complexes.

In the embodiments which belong to the previously defined first subset, complexes are formed by adding the (β2GPI)a to a biological material in order to separate and/or assay and/or quantify nVIC's.

According to a second subset of embodiments of the process according to the invention, use is made of the (β2GPI)n which is naturally and/or initially present in a biological material. It is known that the process of WO 94/18569 yields satisfactory results when the biological material contains free VIC's, that is VIC's which are not attached to the β2GPI which is naturally present in the biological material, with said free VIC's consequently being able to attach themselves to the β2'GPI which is added in accordance with this process. In this process, the response signal therefore increases as the VIC's increase which possess sites which are still free or which may have been released by competition from complexes which are naturally present in the biological material. On the other hand, it is possible to assume, in some cases, for example at the beginning of an infection, that the VIC's are present in a quantity which is low as compared with the (β2GPI)n which is naturally present and that said VIC's are therefore in the main bound to the (β2GPI)n in the form of (β2GPI)n/IC complexes. The test proposed in Application WO 94/18569 may not in that case be meaningful since the VIC's which have thus been complexed may be masked. According to this second subset of the invention, it is proposed, therefore, to observe and/or separate and/or detect and/or quantify IC's which are present in a biological material, in particular in the case where these compounds are in a quantity such that, as compared with the (β2GPI)n which is normally present, they are in the main complexed (or complexable) with at least one of the forms of (β2GPI)n, or else in the case where said IC's cannot be displaced by introducing (β2GPI)a.

Given the fact that, according to this second subset of embodiments according to the invention, no β2GPI has been added, the masking phenomenon of the process of WO 94/18569 is avoided and a response signal is obtained which can increase as a function of the quantities of complex, and therefore of IC, which are contained in the biological material, even in the case of very low quantities of these IC's. Where appropriate, the process can make it possible to detect an initial state of pathology, whereas the earlier process is more appropriate for studying an established pathological state, corresponding, for example, to an excess of IC or to a deficiency of (β2GPI)n or to the natural existence of a form of β2GPI which is non-functional as regards binding to the IC(s).

It is to be noted that these two embodiment subsets are not mutually exclusive.

In order to implement the process according to the invention, IC's can be detected without prior attachment of the β2GPI/IC complex to a support or with attachment of said complex to a support by means of an element which is contained in the complex; in the first case, the detection and/or the quantification is effected in the medium in which the complex is formed, either after the said medium has been attached by means of a physical, chemical or biochemical method, for example to a surface, or without attachment of said medium; in the second case, the support can, advantageously, be a solid support.

In the present description, the term attachment to the support is used without prejudging the time at which the complex is formed.

According to one variant of the invention, the β2GPI/IC complex is held by means of the β2GPI part of the complex, by providing a support with a compound which binds to the said β2GPI part; the part of the complex corresponding to the IC's is then separated/detected/quantified by an appropriate means.

According to another variant of the invention, the β2GPI/IC complex is held by means of the IC part of said complex, by attaching the latter to a support which is provided with a compound which binds to said IC part of the complex; the β2GPI part of the said complex is then detected and/or separated and/or quantified by any appropriate means, advantageously with the aid of (an) antibody(ies) which is/are, in particular, conjugated and is/are specific for β2GPI. The presence in the native state, or the addition, of (a) detergent(s) or lipid(s) can help to attach these antibodies.

According to the invention, the detection can be effected by visualizing and/or counting a structure which is characteristic for the IC, in particular with the eye or by means of microscopy (in particular optical, electron or UV microscopy), by means of detecting the (β2GPI)n which is associated with the IC('s) on these structures, in particular with the aid of a specific labeled antibody, for example an antibody which is conjugated to an enzyme molecule or a fluorescent molecule. The IC('s), which may or may not be complexed, of the biological material can be physically, chemically or biologically attached to a support or be in liquid (in particular acid, ketonic, alcoholic, paraffinic or aldehydic liquid) phase. A double label which is specific for each part can also be employed for detecting the complex, in particular using antibodies which are specific for each part and which are conjugated to 2 different tracers, for example tracers-which fluoresce at different wavelengths. Finally, the IC's in the biological material can be detected or assayed with the aid of an apparatus for analyzing signals such as number, volume, size or shape of particles or structures, for example by means of flow cytometry, in particular.

According to another variant of the invention, the β2GPI/IC complex is held on a support by means of a compound which binds to either the β2GPI part or the IC part of the complex, after which the complex which is attached to said support is separated from said biological material and said (IC/β2GPI) complex is separated and/or detected and/or quantified and/or assayed by recognition of the other part of the complex.

The support is advantageously a solid support: this can be a membrane, for example a nitrocellulose membrane, or a microtitration plate, for example an ELISA microtitration plate, or a microscope slide.

The compound which binds to one of the parts of the complex, an antibody for example, is attached to the support by reacting reactive groups of said compound with the reactive sites of the support. Preferably, this reaction is effected at a temperature of between 0 and 40° C.; the compound which binds to one of the parts of the complex is, advantageously, placed in a buffer which has a pH of between 4.5 and 10.5, preferably of between 6.5 and 7.5; this buffer can advantageously be of the phosphate or acetate type. The support is advantageously maintained in contact with the buffer which contains the compound at a temperature of between 0 and 40° C. for an incubation time of between 30 min and 24 hours. After incubation, the buffer, which has not reacted, is separated from the support and the support is washed, preferably with a buffer which is identical to the previous buffer apart from the fact that it does not contain the abovementioned compound. It may be necessary to saturate the active sites of the support which have not reacted with said compound; in this case, other active groups are caused to react with these active sites; for this purpose, use is advantageously made of a solution of serum albumin, for example bovine serum albumin, or of casein and/or of polyvinylpyrrolidone and/or of gelatin and/or of detergent, which are used simultaneously or successively. After reaction, the support is preferably rinsed and dried.

The support to which the compound which binds to the complex is attached is then placed in contact with a biological material, in particular a liquid, containing the sought-after IC. This biological material is advantageously diluted with the aid of a buffer which gives a pH of between 4.5 and 10.5, preferably of between 5.6 and 7.5. The reaction on the support is preferably effected at a temperature of between 0 and 40° C., advantageously in the vicinity of 37° C., for a period whose duration is between 30 minutes and 24 hours. The solution containing the IC which has not reacted is then advantageously separated from the support; where appropriate, the support is then washed with a saline solution, preferably a buffered saline solution.

In the case where the attachment of the complex to a support is effected by means of the β2 GP I part of the complex, the compound which binds to β2 GP I can be an antibody which recognizes the β2 GP I, or be another protein, for example of viral origin or prokaryotic or eukaryotic cellular origin, such as an albumin or a biological compound, for example a fatty acid, or a lipid, such as a phospholipid, or a chemical compound, for example dextran sulfate, heparin sulfate or a detergent. A free radical or activated radical of the support can bind the β2GPI, sometimes preferentially.

The IC of the β2GPI/IC complex which is bound to the support by the β2GPI can be separated and/or assayed and/or quantified by any known means, such as infectivity, a specific enzyme reaction, a tracer, for example a fluorescent or radioactively labeled tracer, detection of specific nucleic acids by hybridization with a labeled probe, a polymerase chain reaction ("PCR"), an assay, counting, visualization or an optical or (electron) microscopic method. However, the detection and/or assay is/are preferably effected with the aid of an antibody which specifically recognizes proteins of the IC's to be detected. In a known manner, this antibody can be conjugated to an enzymic label, for example peroxidase; the excess of antibody is eliminated by washing; a substrate which is specific for the enzyme which is conjugated to the antibody is then added, in a known manner, with the substrate being transformed, under predetermined conditions, into a colored product; the formation of said colored product indicates the presence of the sought-after IC and enables this IC to be assayed. Use can also be made of an antibody against the IC which is coupled to an isotopic label and then detected radio-metrically.

In the case where the attachment to the support is effected by way of the IC part of the complex, specifically if specific detection is desired, it is visualized with β2GPI which is advantageously conjugated to a label. The IC can be attached to the support either directly or indirectly, for example by way of an antibody. Advantageously, the label can be an enzyme, a radioactive product or a fluorescent product. The IC can be attached to the support by reacting reactive groups of the IC with the reactive sites of the support when the attachment is direct, or by attaching a compound, for example an antibody, to the reactive sites of the support and attaching the IC to said compound which has previously been attached to the support.

While the β2 GP I part of the complex, which complex has been attached by way of a compound which binds the IC part, can be detected by any appropriate means, it is advantageously detected using antibodies which are specific for the β2 GP I and which are, for example, conjugated.

The invention also relates to a solid support for implementing the above-defined process, characterized in that it is suitable for attaching one of the elements of the β2GPI/IC complex or a substance which is suitable for attaching one of the elements of said complex.

The examples given below, purely by way of illustration and not by way of limitation, will help to elucidate the invention. Some have been carried out using a β2'GPI which was obtained in accordance with French Patent Application 2 701 263.

EXAMPLE 1

Visualization of Leishmanias a) Use of fluorescent β2'GPI

A suspension of Leishmania infantum promastigotes, obtained by in-vitro culture on blood agar, is fixed with acetone, at 0° C. for 10 min, on a slide for observation under an optical microscope. The slide is then immersed for 5 min in a phosphate buffer, which is designated "PB" below and which contains monosodium and disodium phosphates at a concentration of 0.01 M and sodium chloride at a concentration of 0.15 M and is at a pH of 7.2±0.1. The β2'GPI is coupled to fluorescein; it is then deposited, at concentrations of 20 μg/ml and 2 μg/ml, on the fixed promastigote suspension, which is then left at 20° C. for 30 min in a moist chamber. The fluorescent β2'GPI which has not been bound is eliminated by immersing the slides for 5 min in two consecutive baths of PB. Fluorescence of the parasites, in particular of their periphery, provides evidence of the formation of complexes and enables these complexes to be visualized and identified.

b) Use of another label for the β2'GPI.

In another experiment, the β2'GPI, which was coupled to alkaline phosphatase, designated "DAP" below, in accordance with Avrameas (Immunochem. (1969) 8, pp. 43–52), reacted with the parasites which were fixed with acetone to slides. The phosphate buffer was replaced so that it did not inhibit the alkaline phosphatase.

The protocol which was implemented, at laboratory temperature, was the following: rehydration of the parasites for 5 min in physiological saline; incubation, at 37° C. for 30 minutes, of the β2'GPI in DAP form and dilution in acetate buffer containing 0.05% of detergent marketed under the name "Triton X100"; 1 wash in 50 mM Tris-HCl (pH=8.2), 50 mM NaCl for 10 min, 1 wash in physiological saline for 10 min, and detection of the alkaline phosphatase activity using the system sold under the name "fast read TR/naphthol". Under these conditions, observation under the optical microscope demonstrates that the β2'GPI still reacts significantly at a concentration of 1 μg/ml.

c) Fluorescence assays on several strains of Leishmania.

Various species of Leishmania were used to demonstrate the interaction between fluorescent β2'GPI and the Leishmanias. The following were tested in this context: *L. infantum, L. marjon, L. guyanensis, L. tronicer, L. donorium* and *L. braziliensis*. All the species demonstrated a significant reaction with fluorescent β2'GPI in the added presence of 0.05% TX100 and 0.25 M NaCl during the reaction.

EXAMPLE 2

The same experiment as in Example 1 was carried out using Toxoplasma gondji [sic], and fluorescence of the parasite was observed with at least 20 μg of β2'GPI/ml.

In the case of these examples 1 and 2, other experiments enabled the sensitivity of detection of the Leishmania and toxoplasmas by the fluorescent β2'GPI to be increased by adding 0.05% TX100 and 0.25 M NaCl to the incubation buffer.

Mixtures of parasites (Leishmanias) and rabbit or human red blood cells were fixed to slides with acetone and then reacted under the above improved conditions. The image which was observed displays a sharp contrast between the strongly fluorescent parasites and the erythocytes [sic], which are very weakly labeled.

As a control, a fluorescent reagent other than β2'GPI, which reagent was composed of rabbit F(ab')c's which were immunopurified and coupled to fluorescein, and which were specific for goat IgG's and did not, therefore, a priori have any specificity for the parasites, was carried out under these above improved conditions, at concentrations of proteins and fluorescein which were identical to those of the fluorescent β2'GPI. This reagent, as well, incidentally, as a pure solution of fluorescein of comparable concentration, only gives a very weak fluorescence on parasites, of the order of the "background noise", when used under the same conditions.

EXAMPLE 3

The same experiment as in Example 1 was carried out on Entamoeba histolytica and fluorescence of the parasite was observed with at least 20 μg of fluorescent β2'GPI/ml.

EXAMPLE 4
Detection of Soluble Leishmania Infantum Antigens

The support used is a micro-ELISA microtitration plate which has 96 wells and a flat bottom, to which Leishmania infantum soluble antigens are attached. This sensitized support is distributed by BIOKEMA-Affinity Products (Switzerland).

A solution of peroxidase-labeled β2'GPI having a concentration of 10 μg/ml is prepared in an acetate buffer which contains 0.05 mol/l acetic acid and sodium acetate, 0.01% bovine serum albumin and 0.05% by weight of "Triton X100", and which is at a pH of 5.6±0.1. 100 μl of this solution are added to each well and the plate is left to incubate at 37° C. for 1 h 30 min. Following this incubation, the contents of the wells of the plate are aspirated. 300 μl of phosphate buffer are introduced into each well and the buffer is then aspirated after a contact time of 2 minutes: this washing operation is repeated 3 times.

100 μl of a solution of o-phenylenediamine OPD, 2 HCl in a sodium citrate buffer are added to each well. The plate is left to incubate at ambient temperature for 30 minutes and the reaction is then stopped by adding 50 μl of 2N $H_2SO_4$ to each well. The absorbance at 492 nm which is obtained at the end of reaction is measured in optical density units (ODU), with this measurement being effected using an automated plate reader.

The obtained results demonstrate recognition of the soluble antigens of Leishmania infantum by the β2'GPI. The same results are obtained when unlabeled β2'GPI is used. In this latter case, the binding is subsequently detected using a peroxidase-labeled anti-β2'GPI monoclonal antibody.

EXAMPLE 5
Binding of β2'GPI to Borrelia Antigens

Use was made of a nitrocellulose membrane onto which Borrelia antigens (gift from I. Nilsson) had been transferred following electrophoresis.

Approximately 40 ng of alkaline phosphatase-coupled β2'GPI, in solution in 1 ml of acetate buffer (0.05 mol/l acetic acid/sodium acetate) which contains 0.1% by weight of gelatin and 0.5% of "TX100", and which has a pH of 5.6±0.1, are reacted, at ambient temperature for 1 h 30 min, with said membrane. The membrane is then rinsed once with a 0.05 mol/l acetate buffer which contains 0.05% by weight of "TX100" and has a pH of 5.6±0.1. The membrane is then rinsed twice with phosphate buffer which contains 0.01 mol/l monosodium and disodium phosphates, 0.15 mol/l sodium chloride, 0.05% by weight of "TX100", and which has a pH of 7.00±0.1. The activity of the alkaline phosphatase is detected in the presence of nitro blue tetrazolium (NBT) and debomo-4-chloro-3-ondolyl phosphate [sic] (BCIP), in a solution containing 50 mM tris (hydroxymethyl) aminomethane, neutralized with hydrochloric acid (Tris-HCl) to pH 8.8, and 0.1 M NaCl. It is seen on the membrane that the β2'GPI makes it possible to detect the presence of *Borrelia afzelii* antigens, in particular those which are thought to indicate pathogenicity, for example p39, osp B, osp A and osp C, in accordance with the terminology used in the publication by Ingrid Nilsson et al. (Serodiagn. Immunother. Infect. Disease, 1993, 5, pp. 245–250). Under the same conditions, there is no reaction with alkaline phosphatase alone.

EXAMPLE 6
Detection of the HBs Antigen of the Hepatitis B Virus

The support which is used is a micro-ELISA microtitration plate which has 96 wells and a flat bottom and which is marketed by "DYNATECH". A 2 μg/ml solution of HIV2 p26 ROD recombinant proteins, supplied by "TRANSGENE" is prepared in a phosphate buffer which contains 0.01 mol/l monosodium and disodium phosphates and 0.15 mol/l sodium chloride and which has a pH of 7.00±0.05. 100 μl of this solution are deposited in the bottom of each well of the microplate. This latter is then incubated at +4° C. for 18 hours. After this, the liquid in each well is aspirated. From 300 to 400 μl of the above-described phosphate buffer, containing 0.05% by weight of the detergent sold under the commercial name "TX100" are then introduced into each well. This buffer is left in contact with the support for 3 minutes and then aspirated; this washing operation is carried out three times.

Three serum samples from healthy donors and four serum samples from patients infected with hepatitis B virus were used. The serum sample is diluted ten, one hundred or one thousand times in acetate buffer which contains 0.05 mol/l acetic acid and sodium acetate, 0.5% by weight of TX100 and 0.01% by weight of bovine serum albumin and which has a pH of 5.6±0.1. 100 μl of solution are deposited in the bottom of each well of the plate, which has been prepared as above. The plate is incubated at 37° C. for a period of 90 minutes. After this incubation, washing is effected by introducing 300 μl of phosphate buffer containing 0.05% by weight TX100 into each well; the buffer solution is left in contact for 2 minutes and then aspirated; this washing operation is repeated four times.

100 μl of a solution of peroxidase-conjugated specific monoclonal antibody against the HBs antigen of the hepatitis B virus are then added to each well. The plate is left to incubate at 37° C. for 60 minutes. Following this incubation, the contents of the wells of the plate are aspirated. 300 μl of phosphate buffer, containing 0.05% by weight of TX100, are introduced into each well and this buffer is then aspirated after a contact time of 2 minutes; this washing operation is repeated five times.

100 μl of a solution of o-phenylenediamine, 2HCL [sic] in a sodium citrate buffer are added to each well. The plate is left to incubate at ambient temperature for 30 minutes and the reaction is then stopped by adding 50 μl of 2N $H_2SO_4$ to each well. The absorbance at 492 nm which is obtained at the end of reaction is measured using an automated plate reader.

The mean of the absorbance obtained for each patient or donor is given in Table 1 (in optical density units multiplied by 1000). HBsAg was efficiently detected in the case of the four patients and was not detected in the case of the three healthy subjects.

TABLE 1

Optical density values (ODU × 1000)

| Serum dilution Origin of the serum | 10 | 100 | 1000 |
|---|---|---|---|
| Healthy donors (3 subjects) | 81 | 72 | 81 |
| | 89 | 64 | 87 |
| | 82 | 66 | 89 |
| Hepatitis B patients (4 subjects) | 2530 | 2493 | 1645 |
| | 696 | 667 | 250 |
| | 2488 | 2555 | 2298 |
| | 1910 | 1280 | 435 |

EXAMPLE 7

The same procedure was used as for Example 6, except that a monoclonal antibody directed against β2'GPI, and termed "8C3" (gift from J. Arvieux), is attached to the support. Similar results were obtained.

In the case of these two examples 6 and 7, it was demonstrated, on the one hand, that the β2 GP I became attached to the support, by detecting it by means of specific antibodies, and it was possible to inhibit, on the other hand, attachment of a (β2 GP I/HBsAg) complex which was present in the serum of a patient suffering from hepatitis B by blocking its attachment to a support, which was prepared for attaching β2 GP I, by means of preincubating the patient's serum, at 37° C. for 30 minutes, with antibodies directed against β2 GP I. These results indicate that the HBsAg of the hepatitis B virus can be recognized by way of the β2 GP I which is present in the plasma, with this latter being, in these assays, bound by the HIV2 p26 ROD or a specific antibody.

EXAMPLE 8

Using the same procedure as that employed in the case of Example 6, the results were positive for detecting surface antigens carried by the LEISHMANIA parasite which was extracted from an infected tissue.

EXAMPLE 9

Formation of a β2GPI/immortalized Lymphocyte Cell Line Cell Complex

The fluorescent β2GPI is incubated with "CEM" cell line cells ($10^6$/ml) which have been pre-rinsed 2 times at 37° C. for 1 h in PBS buffer. After 3 washes in a PBS buffer, the cells are fixed with 2% paraformaldehyde and then analyzed by flow cytofluorometry. Analysis of the binding spectra demonstrates the presence of β2GPI on the majority of the cells, with the amount present depending on the initial dose, which was from 10 to 100 μg/ml.

This binding was observed in the case of other immortalized cell lines, such as the T cell lines: SVPT1 and MOLT4, or the monocyte cell lines: THPI and U937, unlike normal peripheral blood lymphocytes from healthy donors, which were isolated by centrifugation through a cushion of a commercial "Ficoll" solution and then rinsed in PBS.

EXAMPLE 10

Binding of a (β2GPI)n/HBsAg Complex.

In this example, the compound which binds the (β2GPI)n part is human serum albumin (HSA) which has been purified using the method described in WO93/21228. ELISA plates (Nunc Maxisorb) are preloaded with a 1% solution of HSA in 0.1 M Tris glycine, pH 8.8, and then washed thoroughly in PBS, pH 7.2.

An HBsAg+ serum, or a healthy donor serum, is incubated at a 1000 dilution in sodium acetate (50 mM, pH 5.6) at 37° C. for 1 hour and the experiment is conducted as in Example 6 but in the absence of TX100.

The donor serum or the controls without serum do not give any noteworthy signal (<0.05 odu). The HBsAg serum gives a significant signal (≈1.5 odu). HBsAg is consequently captured. If the serum dilution is incubated:

a) in the presence of 800 μg of HSA/ml, the signal is diminished by more than 80%, indicating that the bonding is indeed to the HSA which is attached to the support;

b) in the presence of 4 μg of β2GPI/ml, that is to say only 20 times the quantity of internal β2 originating from the serum, the signal is diminished by almost 40%, signifying that some of the internal complexes are attaching to the support.

If a similar experiment is carried out without preloading the plates, it is observed that HBs is also visualized, being 97% inhibited by a pre-incubation in the presence of HSA and 65% inhibited in the presence of added β2GPI.

EXAMPLE 11

Formation of a Complex of (β2'GPI)a with Mycoplasma Penetrans Proteins

The procedure was as in Example 5 on nitrocellulose strips which contained a few micrograms of IC treated with 2% octyl glucoside, and which were saturated using the EURIS method (14, rue du Chapeau Rouge—34500 BEZIERS (France). The β2GPI, which is labeled in DAP form, is clearly bound to specific antigens which are detected by an immunospecific serum or by a serum which is specific for p 35, in particular, therefore, strongly to the antigens of 35, 40 and 45 Kd and slightly to the 65 Kd antigen.

EXAMPLE 12

Binding of (β'2GPI) [Sic] a to Tetanus Toxoid

Tetanus toxoid (ELOCORIDE, Behring) was transferred, after electrophoresis in a 10% acrylamide gel, to nitrocellulose at the rate of approximately 0.5 to 2 μg/mm².

After saturation of the membranes by the EURIS method, and then 4 rinses with a solution of 50 mM Tris-HCl (pH=8.2), 50 mM NaCl, and 1 rinse in 50 mM Hepes-NaOH (pH 6.8±0.1), 100 ng of DAP in 1 ml of this latter buffer were added to the membranes, which were incubated at 25° C. for one hour in the presence or absence of 10 μg of cardiolipin, referred to as "CL". The membranes were rinsed 4 times with 1 ml of 50 mM Tris-HCl (pH=7.2), 150 mM NaCl.

After visualization as in Example 5, the zone containing the tetanus antigen is the only one which is colored in the presence of CL. In the absence of CL, the reaction does not take place, which indicates the requirement for the presence of CL in order to form the complex under these conditions.

The role of the detergents and/or lipids in the formation of the β2GPI/IC complex was more amply illustrated by the experiments reported below.

From 100 to 200 ng of viral proteins, in solution in water containing 7.5 g of Tris and 14.4 g of glycine per liter and 20% of methanol, are slowly filtered through 2 to 4 mm² of a nitrocellulose membrane (BA84, marketed by "Schleicher and Schull"). The membranes are saturated with the same buffer without methanol but containing 1% HSA; this buffer was obtained as indicated in Example 10. The support is then rinsed thoroughly by four brief prewashes in 50 mM Tris-HCl (pH=8.2), 50 M NaCl, then incubated for from 1 to 4 hours with β2GPI in a reaction medium, and finally washed with after-rinses; the β2GPI is visualized as indicated below.

In a general manner, it is observed that, in the absence of lipid and/or detergent, the β2GPI binds to the albumin which is used for saturation and not to particular viral proteins; however, in the presence of detergent, the reverse is observed, namely that the β2GPI no longer binds to the albumin but binds to particular viral proteins. A phospholipid such as cardiolipin induces such binding.

More precisely, the following results were observed:

A)—The following steps are carried out: reaction with 50 ng of DAP per ml; 4 after-rinses in 50 mM Tris-HCl [sic] (pH=8.2), 50 mM NaCl [sic]; visualization of the DAP in 0.1 M Tris-HCl [sic] (pH=8.8), NBT and BCIP in accordance with the conditions recommended by Merck.

In the absence of detergent in the reaction medium (50 mM Na acetate, pH=5.6), the recombinant proteins HIV₁ p18 and p25 and HIV₂ p26 (TRANSGENE) do not react (white zone of the support), while the recombinant protein HIV gp160 binds DAP slightly and human albumin also reacts (colored background). By contrast, in the presence of 0.5% TX100 or of "Triton 405" or of 0.2% "Tween 20", the albumin no longer displays any reaction while HIV₂ p26 and HIV₁ p8 exhibit a strong reaction. HIV₁ gp160 exhibits a reaction which is greater than that without detergent and HIV₁ p25 exhibits a weak reaction.

B)—Under the same conditions, but in a different reaction medium of 50 mM Tris-HCl [sic] (pH=8.2), only HIV₁ p18 reacts weakly in the presence of detergent.

C)—The following steps are carried out: 1 prewash in 50 mM Hepes, NaOH (pH=6.8): reaction, for 1 hour, in this same buffer, with 100 ng of DAP/ml in the presence or absence of 10 μg of cardiolipin/ml; 4 after-rinses in 0.15 M NaCl, 50 mM Tris-HCl (pH=7.2), 150 mM NaCl and one after-rinse in 0.15 M NaCl and visualization as in A.

None of the 4 HIV proteins reacts without cardiolipin and the 4 react when it is present.

D)—The following steps are carried out: 1 hour of reaction in 50 mM Tris-HCl [sic] (pH=7.6) and in the presence of 1 μg of β2'GPI/ml and 20 μg of CL/ml, 4 washes in the reaction buffer, and visualization of the β2'GPI by 1 hour of incubation in the presence of 54 μg of alkaline phosphatase-coupled monoclonal antibody 8C3/ml in solution in the same buffer to which 0.15 M NaCl and 0.05% "Tween 20" have been added; then 4 rinses with the same solution and 1 rinse with 0.15 M NaCl and visualization as in A.

The 4 viral proteins react, and HIV₁ p25 reacts strongly, while the controls without β2'GPI or without CL do not exhibit any visible reaction.

These examples, among others, indicate that a detergent and/or a lipid, in particular a phospholipid, can promote interaction with the viral proteins, if not participate in said interaction, and that the bond with the albumin is of a different nature since it is sensitive to the detergents which are employed.

It has also been noted that (a) detergent (s) or phospholipid(s) can be added to a stage prior to the presence of β2GPI. It will be noted that the level of phospholipids on the HIV₁ viral proteins is known to be high and that a bond between β2GPI and recombinant HBsAg in the presence of detergent has been described. It follows from this that, in the case of some IC's, and under some environmental conditions, a detergent or a lipid is necessary in order to form the β2GPI/IC complex.

What is claimed is:

1. A method for detecting the presence of an infectious compound in a biological sample which comprises:

detecting the presence of naturally occurring complexes of an infectious compound and β2-glycoprotein I (β2GPI) in the sample;

wherein said infectious compound is present in an infected organism, and not present in a non-infected organism.

2. A method for detecting the amount of an infectious compound in a biological sample which comprises:

detecting the presence of naturally occurring complexes of an infectious compound and β2-glycoprotein I (β2GPI) in the sample; and determining the amount of the infectious compound in the sample based on the level of complex detected;

wherein no exogenous β2-GPI is added to the sample, and wherein said infectious compound is present in an infected organism, and not present in a non-infected organism.

3. The method according to claim 1 wherein at least one viral particle or viral protein is the infectious compound.

4. The method according to claim 2 wherein at least one viral particle or viral protein is the infectious compound.

5. The method according to claim 1 wherein at least one non-viral particle or non-viral protein is the infectious compound.

6. The method according to claim 2 wherein at least one non-viral particle or non-viral protein is the infectious compound.

7. The method according to claim 1 wherein at least one component of a bacterium, a parasite, a mycoplasma or an abnormal animal cell is the infectious compound, and binds said β2 glycoprotein I.

8. The method according to claim 2 wherein at least one component of a bacterium, a parasite, a mycoplasma or an abnormal animal cell is the infectious compound, and binds said β2 glycoprotein I.

9. The method according to claim 1 wherein the complex is attached to a support through said β2GPI, and the infectious compound in the attached complex is detected.

10. The method according to claim 2 wherein the complex is attached to a support through said β2GPI, and the infectious compound in the attached complex is detected.

11. The method according to claim 1 wherein the complex is attached to a support through the infectious compound, said method further comprising the step of separating the sample from the support under conditions wherein the complex remains attached to the support, and the β2GPI in the attached complex is detected.

12. The method according to claim 2 wherein the complex is attached to a support through the infectious compound, said method further comprising the step of separating the sample from the support under conditions wherein the complex remains attached to the support, and the β2GPI in the attached complex is detected.

13. The method according to claim 1 wherein the complex is attached to a support by means of an attachment substance, wherein the attachment substance binds the complex through either the infectious compound or the β2GPI, and wherein said method further comprises the step of separating the sample from the support under conditions wherein the complex remains attached to the support, and either the β2GPI or the infectious compound in the attached complex is detected, whichever is not bound to the attachment substance.

14. The method according to claim 2 wherein the complex is attached to a support by means of an attachment substance, wherein the attachment substance binds the complex through either the infectious compound or the β2GPI, and wherein said method further comprises the step of separating the sample from the support under conditions wherein the complex remains attached to the support, and either the β2GPI or the infectious compound in the attached complex is detected, whichever is not bound to the attachment substance.

15. The method of any one of claims 9–14 wherein said support is a solid support selected from the group consisting of a membrane, a microtitration plate and a microscope slide.

16. The method of any one of claims 9–14 wherein the attachment substance is a protein.

17. The method of claim 16 wherein the protein is an antibody which specifically binds to said β2GPI.

18. The method of claim 16 wherein said protein is $HIV_2p26ROD$ which specifically binds to said β2GPI.

19. The method of claim 3 wherein said at least one viral particle or viral protein is a viral particle or viral protein selected from the group consisting of human immunodeficiency virus 1, human immunodeficiency virus 2, hepatitis B virus and herpes simplex virus.

20. The method of claim 4 wherein said at least one viral particle or viral protein is a viral particle or viral protein selected from the group consisting of human immunodeficiency virus 1, human immunodeficiency virus 2, hepatitis B virus and herpes simplex virus.

21. A method for detecting the presence of an infectious compound of a non-viral infectious agent in a sample of biological material, comprising
    adding exogenous β2-glycoprotein I (β2GPI) to the sample, under conditions whereby any infectious compound of a non-viral infectious agent present in the sample forms a complex with the added β2GPI; and
    detecting the presence of the complex.

22. A method for detecting the amount of an infectious compound of a non-viral infectious agent in a sample of biological material, comprising
    adding exogenous β2-glycoprotein I (β2GPI) to the sample, under conditions whereby any infectious compound of a non-viral infectious agent present in the sample forms a complex with the added β2GPI;
    detecting the presence of the complex; and
    determining the amount of the infectious compound present in the sample based on the level of complex detected.

23. The method according to claim 21 wherein at least one component of a bacterium, a parasite, a mycoplasma or an abnormal animal cell is the infectious compound, and binds said β2 glycoprotein I.

24. The method according to claim 22 wherein at least one component of a bacterium, a parasite, a mycoplasma or an abnormal animal cell is the infectious compound, and binds said β2 glycoprotein I.

25. The method according to claim 21 wherein the complex is attached to a support through said β2GPI, and the infectious compound in the attached complex is detected.

26. The method according to claim 22 wherein the complex is attached to a support through said β2GPI, and the infectious compound in the attached complex is detected.

27. The method according to claim 21 wherein the complex is attached to a support through the infectious compound, said method further comprising the step of separating the sample from the support under conditions wherein the complex remains attached to the support, and the β2GPI in the attached complex is detected.

28. The method according to claim 22 wherein the complex is attached to a support through the infectious compound, said method further comprising the step of separating the sample from the support under conditions wherein the complex remains attached to the support, and the β2GPI in the attached complex is detected.

29. The method according to claim 21 wherein the complex is attached to a support by means of an attachment substance, wherein the attachment substance binds the complex through either the infectious compound or the β2GPI, and wherein said method further comprises the step of separating the sample from the support under conditions wherein the complex remains attached to the support, and either the β2GPI or the infectious compound in the attached complex is detected, whichever is not bound to the attachment substance.

30. The method according to claim 22 wherein the complex is attached to a support by means of an attachment substance, wherein the attachment substance binds the complex through either the infectious compound or the β2GPI, and wherein said method further comprises the step of separating the sample from the support under conditions wherein the complex remains attached to the support, and either the β2GPI or the infectious compound in the attached complex is detected, whichever is not bound to the attachment substance.

31. The method of any one of claims 25–30 wherein said support is a solid support selected from the group consisting of a membrane, a microtitration plate and a microscope slide.

32. The method of any one of claims 29–30 wherein the attachment substance is a protein.

33. The method of claim 32 wherein the protein is an antibody which specifically binds to said β2GPI.

34. The method of claim 33 wherein said protein is HIV$_2$p26ROD which specifically binds to said β2GPI.

35. The method according to claim 21, wherein said β2-glycoprotein I is β2'GPI obtained by eluting an affinity chromatography column from a purification process of albumin from blood plasma, which has a molecular weight of 50,000±3000 daltons.

36. The method according to claim 22, wherein said β2-glycoprotein I is β2'GPI obtained by eluting an affinity chromatography column from a purification process of albumin from blood plasma, which has a molecular weight of 50,000±3000 daltons.

37. The method according to claim 21, wherein at least one of said β2-glycoprotein I and said infectious compound is obtained from an animal or is produced by genetic or chemical engineering.

38. The method according to claim 22, wherein at least one of said β2-glycoprotein I and said infectious compound is obtained from an animal or is produced by genetic or chemical engineering.

39. A method for detecting the presence of an infectious compound of a non-viral infectious agent in a sample of biological material, comprising
adding exogenous β2-glycoprotein I (β2GPI) to the sample, under conditions whereby any infectious compound of a non-viral infectious agent present in the sample forms a complex with the added β2GPI; and detecting the presence of the complex formed between the infectious compound of a non-viral infectious agent and the added β2GPI.

40. A method for detecting the amount of an infectious compound of a non-viral infectious agent in a sample of biological material, comprising adding exogenous β2-glycoprotein I (β2GPI) to the sample, under conditions whereby any infectious compound of a non-viral infectious agent present in the sample forms a complex with the added β2GPI;

detecting the presence of the complex formed between the infectious compound of a non-viral infectious agent and the added β2GPI; and determining the amount of the infectious compound present in the sample based on the level of complex detected.

41. The method according to claim 39 wherein the complex is attached to a support through said β2GPI, and the infectious compound in the attached complex is detected.

42. The method according to claim 40 wherein the complex is attached to a support through said β2GPI, and the infectious compound in the attached complex is detected.

43. The method according to claim 39 wherein the complex is attached to a support through the infectious compound, said method further comprising the step of separating the sample from the support under conditions wherein the complex remains attached to the support, and the β2GPI in the attached complex is detected.

44. The method according to claim 40 wherein the complex is attached to a support through the infectious compound, said method further comprising the step of separating the sample from the support under conditions wherein the complex remains attached to the support, and the β2GPI in the attached complex is detected.

45. The method according to claim 39 wherein the complex is attached to a support by means of an attachment substance, wherein the attachment substance binds the complex through either the infectious compound or the β2GPI, and wherein said method further comprises the step of separating the sample from the support under conditions wherein the complex remains attached to the support, and either the β2GPI or the infectious compound in the attached complex is detected, whichever is not bound to the attachment substance.

46. The method according to claim 40 wherein the complex is attached to a support by means of an attachment substance, wherein the attachment substance binds the complex through either the infectious compound or the β2GPI, and wherein said method further comprises the step of separating the sample from the support under conditions wherein the complex remains attached to the support, and either the β2GPI or the infectious compound in the attached complex is detected, whichever is not bound to the attachment substance.

47. The method of any one of claims 41–46 wherein said support is a solid support selected from the group consisting of a membrane, a microtitration plate and a microscope slide.

48. The method of any one of clams 45–46 wherein the attachment substance is a protein.

49. The method of claim 48 wherein the protein is an antibody which specifically binds to said β2GPI.

50. The method of claim 49 wherein said protein is $HIV_2$p26ROD which specifically binds to said β2GPI.

51. The method according to claim 39, wherein said β2-glycoprotein I is β2'GPI obtained by eluting an affinity chromatography column from a purification process of albumin from blood plasma, which has a molecular weight of 50,000±3000 daltons.

52. The method according to claim 40, wherein said β2-glycoprotein I is β2'GPI obtained by eluting an affinity chromatography column from a purification process of albumin from blood plasma, which has a molecular weight of 50,000±3000 daltons.

53. The method according to claim 39, wherein at least one of said β2-glycoprotein I and said infectious compound is obtained from an animal or is produced by genetic or chemical engineering.

54. The method according to claim 40, wherein at least one of said β2-glycoprotein I and said infectious compound is obtained from an animal or is produced by genetic or chemical engineering.

* * * * *

UNITED STATES PATENT AND TRADEMARK OFFICE
CERTIFICATE OF CORRECTION

PATENT NO. : 6,465,191 B1
DATED : October 15, 2002
INVENTOR(S) : Stefas et al.

It is certified that error appears in the above-identified patent and that said Letters Patent is hereby corrected as shown below:

<u>Title page,</u>
Item [73], reads:

"[73] Assignee: Institut Français de Recherche Scientifiques Pour Le Developpement en Cooperation-ORSTOM, Paris (FR)

should read as:

-- [73] Assignee: Institut de Recherche pour le Développement (IRD), Paris (FR) --

Signed and Sealed this

Seventeenth Day of June, 2003

JAMES E. ROGAN
*Director of the United States Patent and Trademark Office*